(12) United States Patent
Hillisch et al.

(10) Patent No.: US 7,427,610 B2
(45) Date of Patent: Sep. 23, 2008

(54) 2-SUBSTITUTED ESTRA-1,3,5(10)-TRIENE-3-YL SULFAMATE WITH AN ANTI-TUMOUR ACTION

(75) Inventors: Alexander Hillisch, Jena (DE); Olaf Peters, Jena (DE); Christian Gege, Ehingen/Donau (DE); Wilko Regenhardt, Osterode (DE); Dirk Kosemund, Erfurt (DE); Gerhard Siemeister, Berlin (DE); Eberhard Unger, Cospeda (DE); Ulrich Bothe, Berlin (DE)

(73) Assignee: Sterix Limited, Berkshire (GB)

( * ) Notice: Subject to any disclaimer, the term of this patent is extended or adjusted under 35 U.S.C. 154(b) by 0 days.

(21) Appl. No.: 10/546,030

(22) PCT Filed: Feb. 19, 2004

(86) PCT No.: PCT/EP2004/001606

§ 371 (c)(1),
(2), (4) Date: Aug. 18, 2005

(87) PCT Pub. No.: WO2004/074307

PCT Pub. Date: Sep. 2, 2004

(65) Prior Publication Data

US 2006/0160782 A1     Jul. 20, 2006

(30) Foreign Application Priority Data

Feb. 19, 2003   (DE)  ................ 103 07 104

(51) Int. Cl.
*A61K 31/56* (2006.01)
*C07J 1/00* (2006.01)
*C07J 3/00* (2006.01)
*C07J 31/00* (2006.01)

(52) U.S. Cl. ............... 514/182; 552/531; 552/610; 552/614; 552/626

(58) Field of Classification Search ......... 552/531, 552/610, 614, 626
See application file for complete search history.

(56) References Cited

U.S. PATENT DOCUMENTS 6,046,186 A * 4/2000 Tanabe et al. ........... 514/178
6,339,079 B1   1/2002 Kasch et al.
7,071,190 B2   7/2006 Goff et al.
2006/0211670 A1   9/2006 Hillisch et al.

FOREIGN PATENT DOCUMENTS

| DE | 19943708 | 3/2001 |
| WO | WO 98/42729 | 10/1998 |
| WO | WO 99/33858 | 7/1999 |
| WO | WO 0118028 | 3/2001 |

OTHER PUBLICATIONS

MacCarthy-Morrogh L. et al: "Differential Effects of Estrone and Estrone-3-O-Sulfamate Derivatives on Mitotic Arrest, Apoptosis, and Microtubule Assembly in Human Breast Cancer Cells" Cancer Research, vol. 60, pp. 5441-5450, 2000.

Purohit A. et al: "Recent advances in the development of steroid sulphatase inhibitors" Journal of Steroid Biochemistry and Molecular Biology, Elsevier Science Ltd., vol. 69, (1999), pp. 227-238.

Singh A. et al.: "Inhibition of deoxyglucose uptake in MCF-7 breast cancer cells by 2-methoxyestrone and 2-methoxyestrone-3-O-sulfamate" Molecular and Cellular Endocrinology, vol. 160 (2000), pp. 61-66.

* cited by examiner

*Primary Examiner*—Barbara P Badio
(74) *Attorney, Agent, or Firm*—Millen, White, Zelano & Branigan, P.C.

(57) ABSTRACT

Disclosed are compounds of formula I

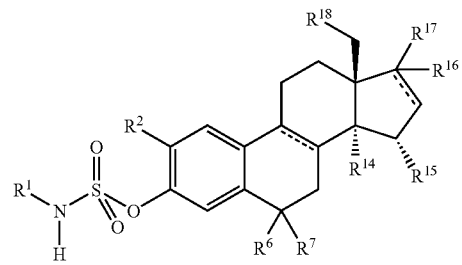

and use thereof in a method of treating a tumor disease that can be influenced positively by the inhibition of tubulin polymerization.

21 Claims, No Drawings

2-SUBSTITUTED ESTRA-1,3,5(10)-TRIENE-3-YL SULFAMATE WITH AN ANTI-TUMOUR ACTION

This application is a 371 of PCT/EP 04/01606 filed on Feb. 19, 2004, and claims priority to DE 10307104.0 filed on Feb. 19, 2003.

This invention relates to 2-substituted estra-1,3,5(10)-trien-3-yl sulfamates and their use for the production of pharmaceutical agents that have an antitumor-active activity.

Microtubuli are organelles that occur in most eukaryotic cells and take over a number of functions there such as mitosis, intracellular movements, cell migration and the manifestation of the cell shape. Microtubuli are polymers that consist of tubulin, which in turn represents a dimer that consists of an α-unit and a β-unit. These heterodimers bind two guanosine triphosphate (GTP) molecules, whereby one of the GTPs is securely bonded and the other is replaceable. In a head-tail arrangement, the heterodimers polymerize into thread-shaped macromolecules, the so-called protofilaments, which in turn pile up into tubular organelles, the microtubuli. Microtubuli are subject to a constant build-up and degradation. The equilibrium between growth and degradation depends on the availability of new GTP-tubulin subunits and the rate of hydrolysis of the second bonded GTPs. On the plus end, new subunits are cultivated; conversely, on the minus end, subunits diffuse outward. It is known that cytotoxic substances such as colchicine, vinblastine, vincristine, taxol, epothilone, podophyllotoxin, steganicin, combretastatin and 2-methoxyestradiol influence the build-up or degradation of mictrotubuli (tubulin polymerization and tubulin depolymerization) and thus are able to influence the cell division in a phase-specific manner. This relates primarily to quick-growing, neoplastic cells, whose growth is largely unaffected by intracellular regulating mechanisms. Active ingredients of this type are in principle suitable for treating malignant tumors.

Fotsis et al. *Nature* 1994 368, 237-239 report, moreover, that 2-methoxyestradiol inhibits the tumor growth and the angiogenesis.

Cushman et al. *J. Med. Chem.* 1995 38, 2041-2049 examine the cytotoxic action as well as the tubulin-polymerization-inhibiting action of 2-methoxyestradiol, and report in *J. Med. Chem.* 1997, 40, 2323-2334, moreover, that 2-alkoxy-6-oximinoestradiol derivatives inhibit the tubulin polymerization as well as the bond of [³H]-colchicine to tubulin. The 2-alkoxy-6-oximinoestradiol derivatives that are mentioned here show comparable activity, relative to the inhibition of tubulin polymerization, such as 2-ethoxyestradiol, which has a higher activity than 2-methoxyestradiol.

In contrast, steroid-3-sulfamates are described in the literature as inhibitors of steroid sulfatase:

WO 93/05064 relates to, i.a., compounds of formula

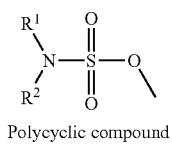

Polycyclic compound whereby $R^1$ and $R^2$, in each case independently of one another, mean hydrogen or a methyl group, provided that at least one of radicals $R^1$ and $R^2$ is an H atom, and the radical-O-polycyclic compound is a 3-sterol, whose sulfate ester can be hydrolyzed by an enzyme with steroid-sulfatase activity. Compounds that are substituted specifically in the 2-position of the steroid skeleton are not explicitly disclosed.

U.S. Pat. No. 6,011,024 is based on WO 93/05064 and covers, e.g., all compounds in which the primary sulfamate function is bonded to a six-membered ring. Compounds that are specifically substituted in the 2-position of the steroid skeleton are in turn not explicitly disclosed.

WO 96/05216 relates to C2-unsubstituted estra-1,3,5(10)-triene-sulfamate derivatives.

WO 96/05217 relates to pharmaceutical compositions that contain active ingredients of general formula

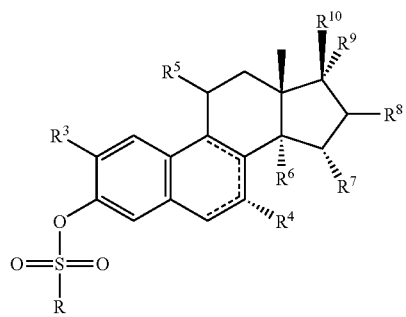

in which $R=NH_2$; $R^3=C_{1-5}$-alkoxy group, OH; $R^8$, $R^9$ and $R^{10}$, independently of one another, =H, OH; $R^9$ and $R^{10}$ together can have the meaning =O. The pharmaceutical compositions that are disclosed therein can be used for female birth control; menopausal HRT and for treatment of gynecological and andrological images of disease, such as breast cancer or prostate cancer.

WO 97/14712 relates to steroid sulfamate derivatives of general formula

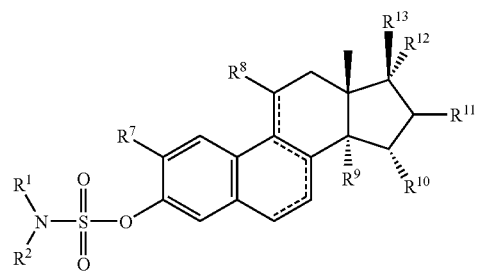

in which $R^1$ can represent an acyl, alkoxycarbonyl, aminocarbonyl, sulfonyl or sulfonamidyl group; $R^2$ can represent a hydrogen atom or a metal atom; $R^7$ and $R^8$, independently of one another, can represent H, OH and $C_{1-5}$-alkoxy; $R^{13}$, $R^{12}$ and $R^{11}$, independently of one another, can represent H or OH.

WO 98/42729 relates to 16-halogen-substituted 1,3,5(10)-triene-3-monosulfamates as well as 3,17β-bissulfamates, which can be alkoxy-substituted at C2. The 16-halogen substitution increases both the sulfatase-inhibiting action and the estrogeneity of the corresponding sulfamate derivatives.

The introduction of a 17-sulfamate function in addition to the 3-sulfamate function drastically reduces the estrogeneity.

WO 98/24802 relates to sulfamates that inhibit the estrone sulfatase. 2-Methoxyestrone sulfamate is explicitly mentioned. As a potential therapeutic application, breast cancer, but not prostate cancer, is mentioned in the description.

Also, WO 99/33858 describes estrone sulfatase inhibitors of formula

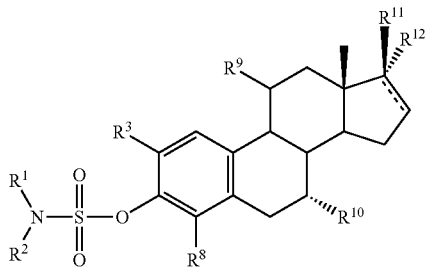

in which R[1] and R[2], independently of one another, represent H, alkyl, or together piperidine, morpholine, piperazine; R[3]=H, CN, NO$_2$, CO$_2$R[4]; R[8]=H, NO$_2$, NR[6]R[7], In the description, breast cancer is mentioned as a possible therapeutic application.

WO 99/64013 relates to a pharmaceutical composition of a sulfamate derivative with a cell signal modifier (such as, e.g., TNFα). 2-Methoxyestrone sulfamate is explicitly claimed as a preferred sulfamate in this combination; but numerous other steroid-3-sulfamates fall under the scope of the general formula. As a mechanism of action for the pharmaceutical compositions according to the invention or for the steroid-3-sulfamates contained therein (preferably with at least one 2-alkoxy substituent), 1) inhibition of glucose absorption in tumor cells, 2) inhibition of tumor angiogenesis, 3) degradation of microtubuli; 4) inducing of apoptosis are described. WO 00/76487 relates to substances that inhibit the TNFα-induced aromatase activity. As such, 2-alkoxyestrone-3-sulfamates, preferably 2-methoxyestrone sulfamate, are claimed.

WO 01/18028 describes non-estrogenic estrone sulfatase-inhibiting N-acyl-18a-substituted steroid-3-sulfamates, such as, e.g., 16α-fluoro-2-methoxy-18a-homoestradiol-(N-acetylsulfamate) or 16α-fluoro-2-methoxy-18a-homoestrone-(N-acetylsulfamate).

In *Cancer* 2000, 85, 983-994, the 2-methoxyestradiol, docetaxel and paclitaxel-induced apoptosis in hepatoma cells and their correlation with reactive oxygen species are compared.

Potter et al. *Int. J. Cancer* 2000, 85, 584-589 examine the action of 2-methoxyestrone sulfamate in comparison to 2-methoxyestrone on the growth of breast cancer cells and induced breast tumors and find that 2-methoxyestrone sulfamate has a significant therapeutic potential for treating breast cancer.

Potter et al. *Molecular and Cellular Endocrinology* 2000, 160, 61-66 examine the inhibition of deoxyglucose absorption in MCF-7 breast cancer cells by 2-methoxyestrone and 2-methoxyestrone-3-sulfamate, which inhibit glucose absorption by 25 to 49% with 10 μm (also 2-methoxyestradiol and 2-methoxyestrone), and it follows that the compounds could have therapeutic potential for inhibiting breast cancer by their capacity to inhibit glucose absorption.

Potter et al. *Cancer Research* 2000, 60, 5441-5450 describe 2-methoxyestrone-sulfamate and 2-ethoxyestrone sulfamate as new antimicrotubulin-active compounds that have in-vitro anti-cancer activity in breast cancer cells and therefore also optionally could be active in vivo. In *J. Steroid Biochem. and Mol. Biol.* 1999, 69, 227-238, it is reported that the inhibition of the steroid sulfatase activity is an important starting point in the treatment of hormone-dependent breast cancer. 2-Methoxyestrone sulfamate, 17-deoxyestrone sulfamate and estrone sulfamate are cited explicitly. Monocyclic or bicyclic, non-steroidal sulfamates namely inhibit the steroid sulfatase, but not as effectively as the corresponding steroid derivatives.

The object of this invention consists in making available additional compounds that effectively inhibit tubulin polymerization.

The object of this invention is therefore achieved according to the invention by the use of 2-substituted estra-1,3,5(10)-trien-3-yl sulfamates of general formula I for the production of a pharmaceutical agent:

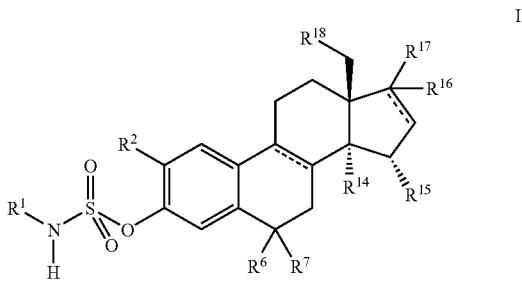

in which the radicals R1 and R2, R6 and R7, R14 and R15, R16 and R17 as well as R18 have the following meaning:
R[1] represents a hydrogen, $C_1$-$C_5$-alkyl or $C_1$-$C_5$-acyl,
R[2] represents $C_1$-$C_5$-alkoxy, $C_1$-$C_5$-alkyl, or a radical —O—$C_nF_mH_o$, whereby n=1, 2, 3, 4, 5 or 6, m>1 and m+o=2n+1,
if R[2] is an alkyl, R[17] can be $C_1$-$C_5$-alkoxy,
R[6] represents hydrogen,
R[7] represents hydrogen, hydroxy; amino, acylamino,
if R[6] and R[7] are not hydrogen, then R[17] can be $C_1$-$C_5$-alkoxy,
or
R[6] and R[7] together represent oxygen, oxime or O($C_1$-$C_5$-alkyl)-oxime,
R[14] and R[15] in each case can mean hydrogen or together a methylene group or an additional bond,
R[16] can mean hydrogen, $C_1$-$C_5$-alkyl, or fluorine,
R[17] can mean hydrogen, fluorine, or,
if R[16] is a hydrogen, R[17] can be a group CHXY, in which X stands for a hydrogen atom, a fluorine, an alkyl radial with 1 to 4 carbon atoms, and Y stands for a hydrogen atom or a fluorine, whereby
    if X is a fluorine, Y is a hydrogen or fluorine, and
    if X is a hydroxy, Y can only be hydrogen or
    X and Y together can be oxygen, or
if R[16] is a fluorine, R[17] can be a hydrogen or a fluorine, or
R[16] and R[17] together can mean a group =CAB, whereby A and B, independently of one another, can mean hydrogen, fluorine or a $C_1$-$C_5$-alkyl group,
R[18] can be a hydrogen atom, or a methyl group,
if R[18] is a methyl group, R[17] can be sulfamate $SO_3$ NHR[1], whereby in the B- and D-ring of the steroid skeleton, the dotted lines can also be up to two double bonds, as well as their pharmaceutically acceptable salts.

In addition, this invention comprises the new substances as pharmaceutical active ingredients, their production, their therapeutic application and the pharmaceutical dispensing forms that contain the new substances.

The compounds of general formula (I) according to the invention or their pharmaceutically acceptable salts can be used for the production of a pharmaceutical agent for treating tumor diseases that can be influenced positively by the inhibition of tubulin polymerization.

It was determined that the 2-substituted estra-1,3,5(10)-trien-3-yl sulfamates according to the invention more greatly inhibit in vitro the tubulin polymerization, surprisingly enough, than 2-methoxyestradiol itself. The compounds according to the invention inhibit the proliferation of tumor cells and also show in-vivo antitumor action. Moreover, the compounds according to the invention have good oral bioavailability.

Alkyl radicals are defined as straight-chain or branched-chain, saturated or unsaturated alkyl radicals. As representatives of straight-chain or branched-chain alkyl groups with 1-5 carbon atoms, for example, methyl, ethyl, propyl, isopropyl, butyl, isobutyl, tert-butyl, pentyl, 1-ethylpropyl, 1-methylbutyl, 1,1-dimethylpropyl, 2-methyl-butyl, 1,2-dimethylpropyl, 3-methylbutyl, 2,2-dimethylpropyl can be mentioned.

For example, allyl, vinyl, propenyl, butenyl, but also ethinyl, propinyl or butinyl stand for unsaturated alkyl radicals.

Acyl radicals mean, for example, formyl, acetyl, propionyl, butyryl, iso-butyryl or valeryl.

A methoxy, ethoxy, n-propoxy, iso-propoxy, n-, iso-, or tert-butoxy, or pentoxy group can stand for a $C_1$-$C_5$-alkoxy radical.

Preferred according to this invention is the use of those compounds of general formula I, in which:
  $R^1$ represents hydrogen or $C_1$-$C_5$-acyl,
  $R^2$ represents methoxy, ethoxy or 2,2,2-trifluoroethoxy,
  $R^6$ and $R^7$ in each case represent hydrogen or together oxime,
  $R^{14}$ and $R^{15}$ in each case represent H or together a methylene group,
  $R^{16}$ represents hydrogen, or fluorine,
  $R^{17}$ represents hydrogen, fluorine, methyl, difluoromethyl, carbaldehyde, vinyl methylene, oximino, hydroxy methyl or
  $R^{16}$ and $R^{17}$ together represent methylene, difluoromethylene or monofluoromethylene,
  $R^{18}$ represents hydrogen, or methyl,
whereby in the B- and D-ring of the steroid skeleton, the dotted lines can also be an 8,9-double bond or a 16,17-double bond.

According to the invention, using separately the compounds that are mentioned below is especially preferred.
  1) 2-Methoxy-estra-1,3,5(10)-trien-3-yl sulfamate (1)
  2) 2-Methoxy-estra-1,3,5(10)-trien-3-yl (N-acetyl)-sulfamate
  3) 2-Methoxy-6-oximino-estra-1,3,5(10)-trien-3-yl sulfamate
  4) 2-Methoxy-estra-1,3,5(10),16-tetraen-3-yl sulfamate
  5) 2-Methoxy-17-(E-vinyl)methylene-estra-1,3,5(10)-trien-3-yl sulfamate (2b)
  6) 2-Ethyl-17β-methoxy-estra-1,3,5(10)-trien-3-yl sulfamate (3)
  7) 2-Methoxy-17(20)-methylene-estra-1,3,5(10)-trien-3-yl sulfamate (4)
  8) 2-Methoxy-17β-methyl-estra-1,3,5(10)-trien-3-yl sulfamate (5)
  9) 2-Methoxy-17(20)-methylene-6-oxo-estra-1,3,5(10)trien-3-yl sulfamate (6)
  10) 2-Methoxy-17(20)-methylene-6-oximino-estra-1,3,5(10)-trien-3-yl sulfamate (7)
  11) 17(20)-Difluoromethylene-2-methoxy-estra-1,3,5(10)-trien-3-yl sulfamate (8)
  12) 17β-Difluoromethyl-2-methoxy-estra-1,3,5(10)trien-3-yl sulfamate (9)
  13) 2-Methoxy-estra-1,3,5(10)-14-tetraen-3-yl sulfamate
  14) 17-Difluoro-2-methoxy-estra-1,3,5(10)-14-tetraen-3-yl sulfamate
  15) 17-Difluoro-2-methoxy-18a-homoestra-1,3,5(10),14-tetraen-3-yl sulfamate
  16) 17β-Carbaldehyde-2-methoxy-estra-1,3,5(10)-trien-3-yl sulfamate (10)
  17) 17β-Carbaldehyde-2-methoxy-18a-homoestra-1,3,5(10)-trien-3-yl sulfamate
  18) 17β-Hydroxymethyl-2-methoxy-estra-1,3,5(10)-trien-3-yl sulfamate (11)
  19) 2,17β-Dimethoxy-6-oximino-18a-homoestra-1,3,5(10)-trien-3-yl sulfamate
  20) 17β-Ethoxy-2-methoxy-6-oximino-18a-homoestra-1,3,5(10)-trien-3-yl sulfamate
  21) 2-Methoxy-6-oxo-18a-homoestra-1,3,5(10)-trien-3-yl sulfamate (12)
  22) 2-Methoxy-6-oximino-18a-homoestra-1,3,5(10)-trien-3-yl sulfamate (13)
  23) 2-Methoxy-6-(O-methyloximino)-18a-homoestra-1,3,5(10)-trien-3-yl sulfamate (14)
  24) 6α-Acetylamino-2-methoxy-18a-homoestra-1,3,5(10)-trien-3-yl sulfamate
  25) 6α-Hydroxy-2-methoxy-18a-homoestra-1,3,5(10)-trien-3-yl sulfamate (15)
  26) 17α-Fluoro-2-methoxy-estra-1,3,5(10)-trien-3-yl sulfamate (16)
  27) 17β-Fluoro-2-methoxy-estra-1,3,5(10)-trien-3-yl sulfamate
  28) 17-Difluoro-2-methoxy-estra-1,3,5(10)-trien-3-yl sulfamate
  29) 17-Difluoro-2-methoxy-6-oximino-estra-1,3,5(10)-trien-3-yl sulfamate
  30) 17-Difluoro-2-methoxy-18a-homoestra-1,3,5(10)-trien-3-yl sulfamate
  31) 17-Difluoro-2-methoxy-6-oximino-18a-homoestra-1,3,5(10)-trien-3-yl sulfamate
  32) 17-Difluoro-2-methoxy-estra-1,3,5(10)-trien-3-yl (N-acetyl)-sulfamate
  33) 2-Methoxy-(E)-17-(oximino)-estra-1,3,5(10)-trien-3-yl sulfamate (17)
  34) 17α-Allyl-17β-hydroxy-2-methoxy-estra-1,3,5(10)trien-3-yl sulfamate (2a)

Subjects of this invention are, moreover, 2-substituted estra-1,3,5(10)-trien-3-yl sulfamates of general formula I,

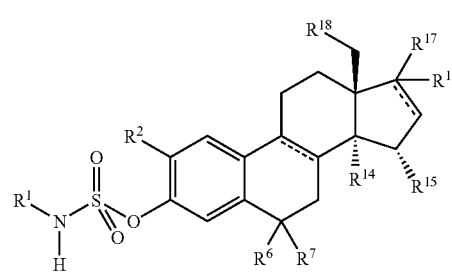

in which radicals R1 and R2, R6 and R7, R14 and R15, R16 and R17 as well as R18 have the following meaning:
  $R^1$ represents a hydrogen, $C_1$-$C_5$-alkyl or $C_1$-$C_5$-acyl,
  $R^2$ represents $C_1$-$C_5$-alkoxy, $C_1$-$C_5$-alkyl or a radical —O—$C_nF_mH_o$, whereby n=1, 2, 3, 4, 5 or 6, m>1 and m+o=2n+1,
  if $R^2$ is an alkyl, $R^{17}$ can be $C_1$-$C_5$-alkoxy, $R^6$ represents hydrogen, $R^7$ represents hydrogen, hydroxy, amino, acylamino, if $R^6$ and $R^7$ are not hydrogen, then $R^{17}$ can be $C_1$-$C_5$-alkoxy, or $R^6$ and $R^7$ together represent oxygen, oxime or O($C_1$-$C_5$-alkyl)-oxime, $R^{14}$ and $R^{15}$ in each case can mean hydrogen or together a methylene group, $R^{16}$ can mean hydrogen, $C_1$-$C_5$-alkyl, or fluorine, $R^{17}$ can mean hydrogen, fluorine, or If $R^{16}$ is a hydrogen, $R^{17}$ can be a group CHXY, in which X stands for a hydrogen atom, a fluorine, an alkyl radical with 1 to 4 carbon atoms, and Y stands for a hydrogen atom or a fluorine, whereby
if X is a fluorine, Y is a hydrogen or fluorine, and
if X is a hydroxy, Y can only be hydrogen or
X and Y together can be oxygen, or if $R^{16}$ is a fluorine, $R^{17}$ can be a hydrogen or a fluorine, or $R^{16}$ and $R^{17}$ together can mean a group =CAB, whereby A and B, independently of one another, can mean hydrogen, fluorine or a $C_1$-$C_5$-alkyl group, $R^{18}$ can be a hydrogen atom, or a methyl group, whereby in the B- and D-ring of the steroid skeleton, the dotted lines can also be up to two double bonds, as well as their pharmaceutically acceptable salts.

The different alkyl, unsaturated alkyl, acyl and alkoxyl radicals correspond to those that are listed for the use according to the invention.

Substituents that are also preferred in the compounds correspond to those that are mentioned in the use according to the invention.

The compounds that are mentioned below are especially preferred according to the invention:

1) 2-Methoxy-estra-1,3,5(10)-trien-3-yl sulfamate
2) 2-Methoxy-estra-1,3,5(10)-trien-3-yl (N-acetyl)-sulfamate
3) 2-Methoxy-6-oximino-estra-1,3,5(10)-trien-3-yl sulfamate
4) 2-Methoxy-estra-1,3,5(10),16-tetraen-3-yl sulfamate
5) 2-Methoxy-17-(E-vinyl)methylene-estra-1,3,5(10)-trien-3-yl sulfamate
6) 2-Ethyl-17β-methoxy-estra-1,3,5(10)-trien-3-yl sulfamate
7) 2-Methoxy-17(20)-methylene-estra-1,3,5(10)-trien-3-yl sulfamate
8) 2-Methoxy-17β-methyl-estra-1,3,5(10)-trien-3-yl sulfamate
9) 2-Methoxy-17(20)-methylene-6-oxo-estra-1,3,5(10)-trien-3-yl sulfamate
10) 2-Methoxy-17(20)-methylene-6-oximino-estra-1,3,5(10)-trien-3-yl sulfamate
11) 17(20)-Difluoromethylene-2-methoxy-estra-1,3,5(10)-trien-3-yl sulfamate
12) 17β-Difluoromethyl-2-methoxy-estra-1,3,5(10)-trien-3-yl sulfamate
13) 17β-Carbaldehyde-2-methoxy-estra-1,3,5(10)-trien-3-yl sulfamate
14) 17β-Carbaldehyde-2-methoxy-18a-homoestra-1,3,5(10)-trien-3-yl sulfamate
15) 17β-Hydroxymethyl-2-methoxy-estra-1,3,5(10)-trien-3-yl sulfamate
16) 2,17β-Dimethoxy-6-oximino-18a-homoestra-1,3,5(10)-trien-3-yl sulfamate
17) 17β-Ethoxy-2-methoxy-6-oximino-18a-homoestra-1,3,5(10)-trien-3-yl sulfamate
18) 2-Methoxy-6-oxo-18a-homoestra-1,3,5(10)-trien-3-yl sulfamate
19) 2-Methoxy-6-oximino-18a-homoestra-1,3,5(10)-trien-3-yl sulfamate
20) 2-Methoxy-6-(O-methyloximino)-18a-homoestra-1,3,5(10)-trien-3-yl sulfamate
21) 6α-Acetylamino-2-methoxy-18a-homoestra-1,3,5(10)-trien-3-yl sulfamate
22) 6α-Hydroxy-2-methoxy-18a-homoestra-1,3,5(10)-trien-3-yl sulfamate
23) 17α-Fluoro-2-methoxy-estra-1,3,5(10)-trien-3-yl sulfamate
24) 17α-Fluoro-2-methoxy-estra-1,3,5(10)-trien-3-yl sulfamate
25) 17-Difluoro-2-methoxy-estra-1,3,5(10)-trien-3-yl sulfamate
26) 17-Difluoro-2-methoxy-6-oximino-estra-1,3,5(10)-trien-3-yl sulfamate
27) 17-Difluoro-2-methoxy-18a-homoestra-1,3,5(10)-trien-3-yl sulfamate
28) 17-Difluoro-2-methoxy-6-oximino-18a-homoestra-1,3,5(10)-trien-3-yl sulfamate
29) 17-Difluoro-2-methoxy-estra-1,3,5(10)-trien-3-yl (N-acetyl)-sulfamate
30) 2-Methoxy-(E)-17-(oximino)-estra-1,3,5(10)-trien-3-yl sulfamate
31) 17α-Allyl-17β-hydroxy-2-methoxy-estra-1,3,5(10) trien-3-yl sulfamate (2a)

Pharmacological Data

1. Inhibition of Tubulin Polymerization

The compounds according to the invention were tested in various models.

The compounds of general formula I according to the invention are distinguished in that they more greatly inhibit tubulin polymerization than 2-methoxyestradiol. The in-vitro testing of the tubulin polymerization influence was performed as follows:

According to Shelanski et al. (Shelanski et al. *Proc. Natl. Acad. Sci. USA* 1973, 70, 765-8), microtubular protein was purified from pig brains via cyclic assembling/disassembling. The buffer system used had the following composition: 20 mmol of PIPES (1,4-piperazine-diethane-sulfonic acid, pKa 6.8), 80 mmol of NaCl, 0.5 mmol of $MgCl_2$, 1 mmol of EGTA (ethylene glycol-bis-(2-aminoethylene)-tetraacetic acid).

For active ingredient testing, protein concentrations of 1 mg/ml (about $10^{-5}$ mmol of tubulin) were used. The determination of protein was carried out according to the Lowry Method (Lowry et al. *J. Biol. Chem.* 1951, 193, 265-75) with bovine serum albumin as a standard. The assembling of microtubuli was carried out in the presence of 0.25 mmol of GTP and heating the samples to 37° C.

The microtubulus formation was examined by means of turbidimetry at a wavelength of 340 nm. The state of equilibrium, in which the microtubular protein exhibits no increase in the assemblate concentration (corresponding to the microtubulus concentration) and the turbidity value no longer exhibits an increase, is typically reached after 20 minutes.

Testing of the active ingredients was carried out by their addition at the beginning of the assembling or in the state of equilibrium. Deviations of turbidity curves from the control characterize its activity. To monitor action and to evaluate the measured turbidity values, a transmission electron microscopic study (CEM 902 A, Zeiss/Oberkochen) of the assemblates was always performed after negative staining with 1% aqueous uranyl acetate.

TABLE 1

| Name | Inhibition of Tubulin Polymerization IC$_{50}$ [μm] |
|---|---|
| 2-Methoxyestradiol | 2.70 |
| (1) | 0.67 |
| (4) | 1.40 |
| (3) | 1.40 |
| (9) | 1.50 |
| (8) | 1.10 |
| (5) | 1.30 |

2. Inhibition of Cell Proliferation

The compounds according to the invention are distinguished by a potent inhibition of cell proliferation.

Cell cultures of the following cell lines were prepared in 96-well microtiter plates:

1. MaTu/ADR multidrug-resistant human breast tumor cells (Epo GmbH Berlin), 5000 cells/well.
2. HCT116 human colon tumor cells (ATCC CCL-247), 3000 cells/well.
3. NCI-H460 human non-small-cell lung cancer cells (ATCC HTB-177), 3000 cells/well.
4. DU145 human prostate tumor cells (ATCC HTB-81), 5000 cells/well.
5. HMVEC human primary dermal microvascular endothelial cells, 7500 cells/well.

After 24 hours of incubation in a cell culture incubator at 37° C., the cells of a microtiter plate were stained with crystal violet (reference plate), while the cells in the test plates were incubated for 4 days with the test substances in the concentrations 0.1-10 μm, as well as with the DMSO solvent by itself (solvent control). The cell proliferation was determined by staining cells with crystal violet. The extinction of the crystal violet was determined by photometry at 595 nm. The percentage of the change in the cell number in the test plates was determined after the extinction values were normalized to the reference plate (0%) and to the solvent control (100%). The semi-maximal inhibition of the cell growth (IC50) was determined as the substance concentration, in which 50% of the cell number of the solvent controls were present.

TABLE 2

| | Inhibition of Cell Proliferation IC50 [μm] | | | | |
|---|---|---|---|---|---|
| Name | NCI-H460 | HCT116 | DU145 | MaTu/ADR | HMVEC |
| Taxol | 0.004 | 0.004 | 0.004 | 0.4 | 0.004 |
| 2-Methoxyestradiol | 1.8 | 1.1 | 1.9 | 0.2 | 2.2 |
| (4) | 0.18 | 0.18 | 0.18 | <0.1 | 0.16 |
| (1) | 0.4 | 0.4 | 0.5 | 0.11 | <0.1 |
| (3) | 0.18 | 0.18 | 0.18 | 0.12 | 0.16 |
| (9) | 0.22 | 0.3 | 0.4 | 0.11 | 0.2 |
| (8) | 0.22 | 0.3 | 0.5 | 0.17 | 0.2 |
| (11) | 0.18 | 0.18 | 0.2 | <0.1 | <0.1 |
| (7) | 0.5 | 0.5 | 0.55 | 0.13 | 0.13 |

Dosage

In general, satisfactory results can be expected when the daily doses comprise a range of 5 μg to 50 mg of the compound according to the invention per kg of body weight. In larger mammals, for example in humans, a recommended daily dose is in the range of 10 μg to 30 mg per kg of body weight.

Suitable dosages for the compounds according to the invention are from 0.005 to 50 mg per day per kg of body weight, depending on the age and constitution of the patient, whereby the necessary daily dose can be administered one or more times.

Based on the special depot action of the estrogen-sulfamates, the compounds according to the invention can, however, also be administered at greater intervals than once per day.

The formulation of the pharmaceutical preparations based on the new compounds is carried out in a way that is known in the art, by the active ingredient being processed with the vehicles, fillers, substances that influence decomposition, binding agents, moisturizing agents, lubricants, absorbing agents, diluents, flavoring correctives, coloring agents, etc., that are commonly used in galenicals and converted into the desired form of administration. In this case, reference is made to Remington's Pharmaceutical Science, 15$^{th}$ Edition, Mack Publishing Company, East Pennsylvania (1980).

For oral administration, in particular tablets, coated tablets, capsules, pills, powders, granulates, lozenges, suspensions, emulsions or solutions are suitable.

For parenteral administration, injection and infusion preparations are possible.

For intraarticular injection, correspondingly prepared crystal suspensions can be used.

For intramuscular injection, aqueous and oily injection solutions or suspensions and corresponding depot preparations can be used.

For rectal administration, the new compounds can be used in the form of suppositories, capsules, solutions (e.g., in the form of enemas) and ointments both for systemic and for local therapy.

For pulmonary administration of the new compounds, the latter can be used in the form of aerosols and inhalants.

For topical application, formulations in gels, ointments, fatty ointments, creams, pastes, powders, milks and tinctures are possible. The dosage of the compounds of general formula I should be 0.01%-20% in these preparations to achieve an adequate pharmacological action.

This invention comprises the use of the compounds of general formula I according to the invention for the production of a pharmaceutical agent, in particular for treating tumor diseases that can be influenced positively by the inhibition of tubulin polymerization.

The compounds of general formula I according to the invention are preferably used for the production of a pharmaceutical agent for treating tumor diseases of the male and female gonads, male and female sex organs including the mammary glands, in particular of prostate cancer or breast cancer.

This invention also relates to pharmaceutical compositions that contain at least one especially preferred compound according to the invention, optionally in the form of a pharmaceutically/pharmacologically compatible salt, without or together with pharmaceutically compatible adjuvants and/or vehicles.

These pharmaceutical compositions and pharmaceutical agents can be provided for oral, rectal, vaginal, subcutaneous, percutaneous, intravenous or intramuscular administration. In addition to commonly used vehicles and/or diluents, they contain at least one especially preferred compound according to the invention.

The pharmaceutical agents of the invention are produced with commonly used solid or liquid vehicles or diluents and the commonly used pharmaceutical-technical adjuvants corresponding to the desired type of administration at a suitable dosage in a known way. The preferred preparations consist in a dispensing form that is suitable for oral administration. Such dispensing forms are, for example, tablets, film tablets, coated tablets, capsules, pills, powders, solutions or suspensions or else depot forms.

The pharmaceutical compositions that contain at least one of the compounds according to the invention are preferably administered orally.

Parenteral preparations such as injection solutions are also considered. In addition, for example, suppositories and agents for vaginal application can also be mentioned as preparations.

Corresponding tablets can be obtained by, for example, mixing active ingredient with known adjuvants, for example inert diluents such as dextrose, sugar, sorbitol, mannitol, polyvinyl pyrrolidone, explosives such as corn starch or alginic acid, binding agents such as starch or gelatin, lubricants such as magnesium stearate or talc and/or agents for achieving a depot effect such as carboxyl polymethylene, carboxyl methyl cellulose, cellulose acetate phthalate or polyvinyl acetate. The tablets can also consist of several layers.

Coated tablets accordingly can be produced by coating cores, which are produced analogously to the tablets, with agents that are commonly used in tablet coatings, for example, polyvinyl pyrrolidone or shellac, gum Arabic, talc, titanium oxide, or sugar. In this case, the shell of the coated tablets can also consist of several layers, whereby the adjuvants that are mentioned above in the tablets can be used.

Solutions or suspensions with the compounds of general formula I according to the invention can contain additional taste-improving agents such as saccharine, cyclamate or sugar, as well as, e.g., flavoring substances such as vanilla or orange extract. In addition, they can contain suspending adjuvants such as sodium carboxy methyl cellulose or preservatives such as p-hydroxybenzoates.

Capsules that contain the compounds of general formula I can be produced by, for example, the compound(s) of general formula I being mixed with an inert vehicle such as lactose or sorbitol and encapsulated in gelatin capsules.

Suitable suppositories can be produced by, for example, mixing with vehicles that are provided for this purpose, such as neutral fats or polyethylene glycol or derivatives thereof.

For therapy of prostate cancer, the compounds according to the invention can be administered in combination with one or more of the following active ingredients:

1) Antiandrogens such as CPA, flutamide, casodex, etc.
2) Gonadotrophic hormone (GnRH) agonists
3) 5α-Reductase inhibitors such as finasteride
4) Cytostatic agents
5) VEGF-kinase inhibitors
6) Antigestagens
7) Antiestrogens
8) Antisense oligonucleotides
9) EGF antibodies
10) Estrogens Moreover, the compounds of general formula I according to the invention can be used for therapy and prophylaxis of other pathologic conditions that are not mentioned above.

The compounds of general formula I according to the invention can be produced as described below:

General Synthesis Part

The functionalization of C-atom 2 of an estra-1,3,5(10)-trien-17-one derivative is preferably carried out by Friedel-Crafts acylation as described in the literature (T. Nambara et al. *Chem. Pharm. Bull.* 1979, 18, 474-480).

After changing the protective group in 3-position, a 2-carboxy-estra-1,3,5(10)-trien-17-one is generated by Baeyer-Villiger oxidation (M. B. Smith, J. March, *March's Advanced Organic Chemistry*, 5$^{th}$ Edition, Wiley Sons 2001, 1417-1418 and literature cited there). The ester is saponified and converted with the corresponding alkyl halide under basic conditions into a 2-alkyl ether. Alternately, the 17-ketone as known can now be reduced and etherified. The cleavage of the protective group in 3-position is carried out as described in the literature (T. W. Greene, P. G. M. Wuts, *Protective Groups in Organic Synthesis*, Wiley & Sons, 1999, 249-275). This process or other processes known from the literature (P. N. Rao, J. W. Cessac, *Steroids* 2002, 67, 1065-1070 and literature cited there) can be used according to the 18a-homo derivatives.

The 2-acyl derivatives that are preferably obtained by Friedel-Crafts acylation can be converted by reduction with sodium borohydride and subsequent hydrogenation into the corresponding 2-alkyl derivatives.

The 2-hydroxylation, starting from compounds of general formula II ($R_2$=H),

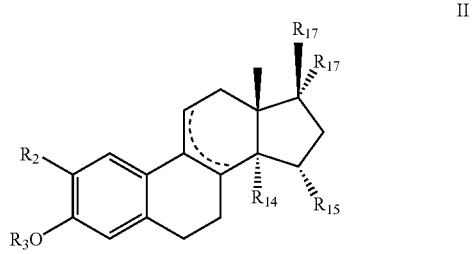

in which $R_{14}$ and $R_{15}$ together form a methylene bridge or which have additional double bonds in the steroid skeleton, is carried out by ortho-metallation, whereby preferably an ether protective group (e.g., H. E. Paaren, S. R. Duff, U.S. Pat. No. 6,448,419 and literature cited there) or a carbamate protective group (V. Snieckus, *Chem. Rev.* 1990, 90, 879-933) is used for $R_3$ as an ortho-directing protective group. The electrophilic substitution is carried out after 2-lithiation with trialkyl borate and then basic oxidation with hydrogen peroxide. The selectively obtained 2-hydroxy group can then be converted into a 2-alkoxy compound in a known way (Z. Wang, M. Cushman, *Synth. Commun.* 1998, 28, 4431) and deprived of protection. Subsequent Oppenauer oxidation (C. Djerassi, *Org. React.* 1951, 6, 207, S. Schwarz et al. *Pharmazie [Pharmaceutics]* 2001, 56, 843-849) yields the 17-keto compounds, which can be further functionalized and reacted as known to form the sulfamates.

Starting from the 2-functionalized 17-keto derivatives, 17-oxiranes (M. Hübner, I. Noack, *J. prakt. Chem.* 1972, 314, 667) and from them the corresponding 17-formyl derivatives (M. Hübner, K. Ponsold, *Z. Chem.* 1982, 22, 186) or 17-monofluorinated methyl derivatives (B. Menzenbach et al., DE 10043846) can be produced.

The corresponding 17-oxime, 17-alkylene (so-called Wittig reaction, see, e.g., S. Schwarz et al. *Pharmazie* 2001, 56, 843-849), 17-difluoromethylene (Wadsworth-Emmons Reaction, S. R. Piettre, L. Cabanas, *Tetrahedron Lett.* 1996, 37, 5881-4884), 17-deoxo, 17β-alkyl, and 17β-hydroxymethyl derivatives can also be produced from the 2-functionalized derivatives (e.g., R. H. Peters et al., *J. Med. Chem.* 1989, 32, 1642; G. E. Agoston et al. WO 02/42319) and then sulfamoylated in 3-position.

According to Cushman et al. (*J. Med. Chem.* 1997, 40, 2323), the synthesis of 6-functionalized estrogen derivatives is carried out by oxidation of the acetyl-protected estrogen derivative with chromium trioxide.

17-Fluorinated derivatives can be produced from the corresponding 17-oxo or 17-hydroxy derivatives with diethylamino-sulfur trifluoride (M. Hudlicky, *Org. Reactions* 1988, 35, 513; J. T. Welch, *Fluorine in Bioorganic Chemistry* 1991, John Wiley, New York; S. Rozen et al. *Tetrahedron Lett.* 1979, 20, 1823-1826) and then sulfamoylated.

This invention is explained in more detail based on the examples below, without being limited thereto:

Production Process

General Synthesis Instructions 1 for the Production of Sulfamates

One equivalent of an estra-1,3,5(10)-triene derivative in methylene chloride is dissolved or suspended while being stirred and mixed with 5 equivalents of 2,6-di-tert-butylpyridine. Then, 10 equivalents of sulfamoyl chloride are added under argon and stirred at room temperature. The solution is stirred until conversion is completed (TLC monitoring, 1-5 hours) and then mixed with water. In acid-sensitive compounds, buffering is done in advance with about 10 equivalents of triethylamine. The aqueous phase is extracted several times with dichloromethane or ethyl acetate. The combined organic phases are dried on sodium sulfate and concentrated by evaporation in a vacuum and then purified by flash chromatography.

General Synthesis Instructions 2 for Acylation of Sulfamates

One equivalent of the estra-1,3,5(10)-triene-sulfamate or bissulfamate is dissolved in pyridine and mixed with 5 equivalents of anhydride while being cooled with ice (0 to 5° C.). Stirring is continued for 1 hour at room temperature and then mixed with water. The aqueous phase is extracted several times with dichloromethane or ethyl acetate. The combined organic phases are washed with 6N hydrochloric acid and then with water and sodium chloride solution. Then, it is dried on sodium sulfate and concentrated by evaporation in a vacuum and then purified by flash chromatography.

EXAMPLE 1

2-Methoxy-estra-1,3,5(10)-trien-3-yl Sulfamate (1)

1.48 g of 3-hydroxy-2-methoxy-estra-1,3,5(10)-triene was reacted to form the product according to general synthesis instructions 1 and then purified by flash chromatography (toluene/ethyl acetate=19:1→10:1). 1.69 g (89%) of 2-methoxy-estra-1,3,5(10)-trien-3-yl sulfamate (1) was obtained as an amorphous powder.

$^1$H-NMR (CDCl$_3$): δ=0.75 (s, 3H; 18-CH$_3$), 2.76-2.84 (m, 2H; 6-CH$_2$), 3.87 (s, 3H; 2-OCH$_3$), 4.96 (s, 2H; NH$_2$), 6.94, 7.03 (2 s, 2H; 1-H, 4-H).

EXAMPLE 2

17α-Allyl-17β-hydroxy-2-methoxy-estra-1,3,5(10)-trien-3-yl Sulfamate (2a) and 2-Methoxy-17-(E-vinyl)methylene-estra-1,3,5(10)trien-3-yl Sulfamate (2b)

622 mg of 3-hydroxy-2-methoxy-estra-1,3,5(10)-trien-17-one was dissolved in 35 ml of absolute tetrahydrofuran under argon and mixed at −70° C. with 20 ml of allylmagnesium bromide solution (1 M in diethyl ether). Then, it was allowed to come to room temperature and poured into aqueous ammonium chloride solution after 3 hours and extracted with ethyl acetate (2×). The combined organic phases were washed with saturated common salt solution, dried and concentrated by evaporation in a rotary evaporator. Flash chromatography (cyclohexane/ethyl acetate=5:1→3:1) yielded 663 mg (94%) of 17α-allyl-3,17β-dihydroxy-2-methoxy-estra-1,3,5(10)-triene as colorless crystals.

$^1$H-NMR (CDCl$_3$): δ=0.94 (s, 3H; 18-CH$_3$), 3.86 (s, 3H; 2-OCH$_3$), 5.16-5.23 (m, 1H; C=CH$_2$), 5.44 (s, 1H; OH), 5.96-6.06 (m, 1H; —CH=C), 6.63, 6.79 (2 s, 2H; 1-H, 4-H).

104 mg of 17α-allyl-3,17β-dihydroxy-2-methoxy-estra-1,3,5(10)-triene was reacted to form the products according to general synthesis instructions 1 and then purified by flash chromatography (cyclohexane/ethyl acetate=15:1→10:1→5:1). In addition to starting material and dewatered starting material, 28 mg (22%) of 17α-allyl-17β-hydroxy-2-methoxy-estra-1,3,5(10)-trien-3-yl sulfamate (2a) as well as 36 mg (29%) of 2-methoxy-17-(E-vinyl)methylene-estra-1,3,5(10)-trien-3-yl sulfamate (2b) were obtained as an amorphous powder.

2a: $^1$H-NMR (CDCl$_3$): δ=0.94 (s, 3H; 18-CH$_3$), 2.78-2.82 (m, 2H; 6-CH$_2$), 3.87 (s, 3H; 2-OCH$_3$), 5.01 (s, 2H; NH$_2$), 5.16-5.24 (m, 1H; C=CH$_2$), 5.95-6.07 (m, 1H; —CH=C), 6.92, 7.03 (2 s, 2H; 1-H, 4-H).

2b: $^1$H-NMR (CDCl$_3$): δ=0.83 (s, 3H; 18-CH$_3$), 2.77-2.84 (m, 2H; 6-CH$_2$), 3.87 (s, 3H; 2-OCH$_3$), 4.98-5.13 (m, 4H, 22-CH$_2$, NH$_2$), 5.76 (d, $^3$J=10.8 Hz, 1H; 20-CH=), 6.40-6.50 (m, 1H; 21-CH=), 6.94, 7.03 (2 s, 2H; 1-H, 4-H)

EXAMPLE 3

2-Ethyl-17β-methoxy-estra-1,3,5(10)-trien-3-yl sulfamate (3)

362 mg of 2-acetyl-3-benzyloxy-estra-1,3,5(10)-trien-17-one was dissolved in 150 ml of tetrahydrofuran/methanol 10/1, mixed with sodium borohydride and stirred for 3 hours at room temperature, mixed with acetic acid and concentrated by evaporation in a rotary evaporator. The residue was mixed with water and extracted with dichloromethane (2×). The combined organic phases were washed with saturated sodium bicarbonate solution, dried and concentrated by evaporation in a rotary evaporator. The residue was dissolved in 5 ml of absolute dimethylformamide under argon, mixed with 0.32 g of sodium hydride (~50%) and then with 1.5 ml of methyl iodide and stirred overnight at room temperature. After the addition of water, it was extracted with ethyl acetate (2×). The combined organic phases were washed with water and then with saturated common salt solution, dried and concentrated by evaporation in a rotary evaporator. Flash chromatography (toluene/ethyl acetate=60:1) yielded 301 mg (77%) of 2-(1-methoxyethyl)-3-benzyloxy-17β-methoxy-estra-1,3,5(10)-triene as colorless crystals.

290 mg of 2-(1-methoxyethyl)-3-benzyloxy-17β-methoxy-estra-1,3,5(10)-triene was dissolved in 20 ml each of ethyl acetate and dichloromethane and then mixed with 3 drops of acetic acid and 110 mg of palladium on activated carbon (10%). The hydrogenation was carried out under normal pressure over 8 hours. The catalyst was filtered out, and the solution was concentrated by evaporation in a rotary evaporator and co-evaporated several times with toluene. Flash chromatography (toluene/acetone=80:1) yielded 220 mg (98%) of 2-ethyl-3-hydroxy-17β-methoxy-estra-1,3,5(10)-triene as a colorless foam.

$^1$H-NMR (CDCl$_3$): δ=0.79 (s, 3H; 18-CH$_3$), 1.22 (t, $^3$J=7.6 Hz, 3H; CH$_3$), 2.59 (q, $^3$J=7.6 Hz, 2H; 2-CH$_2$Me), 2.76-2.79 (m, 2H; 6-CH$_2$), 3.13 (t, $^3$J≈8.4 Hz, 1H; 17α-H), 3.38 (s, 3H; 17β-OCH$_3$), 4.57 (s, 1H; OH), 6.48, 7.04 (2 s, 2H; 1-H, 4-H).

93 mg of 2-ethyl-3-hydroxy-17β-methoxy-estra-1,3,5 (10)-triene was reacted to form the product according to general synthesis instructions 1 and then purified by flash chromatography (toluene/ethyl acetate=20:1→10:1). 110 mg (94%) of 2-ethyl-17β-methoxy-estra-1,3,5(10)-trien-3-yl sulfamate (3) was obtained as colorless crystals.

$^1$H-NMR (CDCl$_3$): δ=0.78 (s, 3H; 18-CH$_3$), 1.22 (t, $^3$J≈7.6 Hz, 3H; CH$_3$), 2.69 (q, $^3$J=7.6 Hz, 2H; 2-CH$_2$Me), 2.81-2.84 (m, 2H; 6-CH$_2$), 3.31 (t, $^3$J≈8.2 Hz, 1H; 17α-H), 3.37 (s, 3H; 17β-OCH$_3$), 4.97 (s, 2H; NH$_2$), 7.07, 7.18 (2 s, 2H; 1-H, 4-H).

EXAMPLE 4

2-Methoxy-17(20)-methyleneestra-1,3,5(10)-trien-3-yl Sulfamate (4)

1.6 g of sodium hydride (55%) was added to a solution that consists of 11.8 g of methyltriphenyl phosphonium bromide in 50 ml of absolute dimethyl sulfoxide at room temperature. After 30 minutes, a solution that consists of 1.00 g of 3-hydroxy-2-methoxy-estra-1,3,5(10)-trien-17-one in 50 ml of absolute dimethyl sulfoxide was added thereto and then heated to 70° C. After 1 hour, it was cooled to room temperature, mixed with water and extracted with diethyl ether (3×). The combined organic phases were washed with water, dried and concentrated by evaporation in a rotary evaporator. Flash chromatography (toluene/ethyl acetate=40:1) yielded 979 mg (98%) of 3-hydroxy-2-methoxy-17(20)-methylene-estra-1,3,5(10)-triene as colorless crystals.

$^1$H-NMR (CDCl$_3$): δ=0.83 (s, 3H; 18-CH$_3$), 3.86 (s, 3H; 2-OCH$_3$), 4.67 (t, 1H; =CH$_2$), 5.41 (s, 1H; 3-OH), 6.64, 6.80 (2 s, 2H; 1-H, 4-H).

100 mg of 3-hydroxy-2-methoxy-17(20)-methylene-estra-1,3,5(10)-triene was reacted to form the product according to general synthesis instructions 1 (base, but in excess relative to sulfamoyl chloride) and then purified by flash chromatography (toluene/ethyl acetate=15:1→10:1). 90 mg (72%) of 2-methoxy-17(20)-methylene-estra-1,3,5(10)-trien-3-yl sulfamate (4) was obtained as a colorless powder.

$^1$H-NMR (CDCl$_3$): δ=0.83 (s, 3H; 18-CH$_3$), 2.79-2.81 (m, 2H; 6-CH$_2$), 3.87 (s, 3H; 2-OCH$_3$), 4.68 (t, $^2$J=1.2 Hz, 2H; 20-CH$_2$), 5.01 (s, 2H; NH$_2$), 6.94, 7.03 (2 s, 2H; 1-H, 4-H).

EXAMPLE 5

2-Methoxy-17β-methyl-estra-1,3,5(10)-trien-3-yl Sulfamate (5)

108 mg of 3-hydroxy-2-methoxy-17β-methyl-estra-1,3,5 (10)-triene (obtained by hydrogenation of 3-hydroxy-2-methoxy-17(20)-methylene-estra-1,3,5(10)-triene) was reacted to form the product according to general synthesis instructions 1 and then purified by flash chromatography (toluene/ethyl acetate=30:1→15:1). 124 mg (91%) of 2-methoxy-17β-methyl-estra-1,3,5(10)-trien-3-yl sulfamate (5) was obtained as colorless crystals.

$^1$H-NMR (CDCl$_3$): δ=0.59 (s, 3H; 18-CH$_3$), 0.88 (d, $^3$J=7.0 Hz, 3H; 17-CH$_3$), 2.77-2.80 (m, 2H; 6-CH$_2$), 3.86 (s, 3H; 2-OCH$_3$), 5.01 (s, 2H; NH$_2$), 6.93, 7.02 (2 s, 2H; 1-H, 4-H).

EXAMPLE 6

2-Methoxy-17(20)-methylene-6-oxo-estra-1,3,5(10)-trien-3-yl Sulfamate (6)

3-Acetoxy-2-methoxy-17(20)-methylene-6-oxo-estra-1,3,5(10)-triene was oxidized in 6-position with chromium trioxide in acetic acid at 10° C. in a yield of 48% and then the acetyl group was cleaved off quantitatively by sodium methanolate in methanol. Sulfamoylation of 72 mg of this intermediate product according to general synthesis instructions 1 and subsequent flash chromatography (toluene/ethyl acetate=5:1) yielded 2-methoxy-17(20)-methylene-6-oxo-estra-1,3,5(10)-trien-3-yl sulfamate (6) in a yield of 75% as colorless crystals.

$^1$H-NMR (CDCl$_3$): δ=0.83 (s, 3H; 18-CH$_3$), 3.98 (s, 3H; 2-OCH$_3$), 4.71 (s, 2H; =CH$_2$), 5.23 (s, 2H; NH$_2$), 7.00, 7.98 (2 s, 2H; 1-H, 4-H).

EXAMPLE 7

2-Methoxy-17(20)-methylene-6-oximino-estra-1,3,5 (10)-trien-3-yl Sulfamate (7)

55 mg of 2-methoxy-17(20)-methylene-6-oxo-estra-1,3,5 (10)-trien-3-yl sulfamate (6) was heated with 70 mg of hydroxylamine-hydrochloride and 100 mg of sodium bicarbonate in 3 ml of methanol for 3 hours to 60° C. Then, it was cooled to room temperature, mixed with water and extracted with ethyl acetate (3×). The combined organic phases were washed with saturated sodium chloride solution, dried and concentrated by evaporation in a rotary evaporator. Flash chromatography (toluene/acetone=8.1→5:1) yielded 26 mg (46%) of 2-methoxy-17(20)-methylene-6-oximino-estra-1,3,5(10)-trien-3-yl sulfamate (7) as a white amorphous solid as well as as by-product 3-hydroxy-2-methoxy-17(20)-methylene-6-oximino-estra-1,3,5(10)-triene.

$^1$H-NMR (acetone-d$_6$): δ=0.71 (s, 3H; 18-CH$_3$), 3.78 (s, 3H; 2-OCH$_3$), 4.55 (d, 2H; =CH$_2$), 6.94, 7.74 (2 s, 2H; 1-H, 4-H).

EXAMPLE 8

17(20)Difluoromethylene-2-methoxy-estra-1,3,5 (10)-trien-3-yl Sulfamate (8)

6.4 ml of a tert-butyllithium solution (1.5 M in pentane) was added in drops at −70° C. while being stirred to a solution that consists of 1.53 ml of diethyl(difluoro-methyl)phosphonate in 10 ml of absolute 1,2-dimethoxyethane. After 20 minutes, a solution that consists of 733 mg of 3-hydroxy-2-methoxy-estra-1,3,5(10)-trien-17-one in 20 ml of 1,2-dimethoxyethane was added in drops thereto and then the cooling bath was removed, and the reaction solution was stirred for another 30 minutes. Then, it was refluxed for 2 hours, cooled to room temperature and mixed with aqueous ammonium chloride solution and extracted with ethyl acetate (3×). The combined organic phases were washed with saturated common salt solution, dried and concentrated by evaporation in a rotary evaporator. Flash chromatography (cyclohexane/ethyl acetate=20:1→15:1→10:1) yielded 514 mg (63%) of 17(20)-difluoromethylene-3-hydroxy-2-methoxy-estra-1,3,5(10)-triene as an amorphous solid.

$^1$H-NMR (CDCl$_3$): δ=0.92 (s, 3H; 18-CH$_3$), 3.86 (s, 3H; 2-OCH$_3$), 5.43 (s, 1H; 3-OH); 6.64, 6.78 (2 s, 2H; 1-H, 4-H)-$^{19}$F-NMR (CDCl$_3$): δ=−91.1, −96.4 (2d, $^2$J=68.9 Hz).

113 mg of 17(20)-difluoromethylene-3-hydroxy-2-methoxy-estra-1,3,5(10)-triene was reacted to form the product according to general synthesis instructions 1 (base, but in excess relative to sulfamoyl chloride) and then purified by flash chromatography (cyclohexane/ethyl acetate=3:1→2:1). 101 mg (72%) of 17(20)-difluoromethylene-2-methoxy-estra-1,3,5((10)-trien-3-yl sulfamate (8) was obtained as an amorphous powder.

$^1$H-NMR (CDCl$_3$): δ=0.93 (s, 3H; 18-CH$_3$), 3.88 (s, 3H; 2-OCH$_3$), 4.96 (s, 2H; NH$_2$), 6.92, 7.03 (2 s, 2H; 1-H, 4-H)-$^{19}$F-NMR (CDCl$_3$): δ=−91.9, −96.2 (2d, $^2$J=6.89 Hz).

EXAMPLE 9

17β-Difluoromethyl-2-methoxy-estra-1,3,5(10)-trien-3-yl Sulfamate (9)

200 mg of 17(20)-difluoromethylene-3-hydroxy-2-methoxy-estra-1,3,5(10)-triene was dissolved in 10 ml of ethyl acetate and then mixed with 3 drops of acetic acid and 70 mg of palladium on activated carbon (10%). The hydrogenation was carried out under normal pressure overnight. The catalyst was filtered out, and the solution was concentrated by evaporation in a rotary evaporator and co-evaporated several times with toluene. Flash chromatography (cyclohexane/ethyl acetate=10:1→5:1) yielded 150 mg (74%) of 17β-difluoromethyl-3-hydroxy-2-methoxy-estra-1,3,5(10)-triene as a colorless solid.

$^1$H-NMR (CDCl$_3$): δ=0.81 (s, 3H; 18-CH$_3$), 3.85 (s, 3H; 2-OCH$_3$), 5.42 (s, 1H; OH), 5.73 (td, 1H; CHF$_2$), 6.63, 6.77 (2 s, 2H; 1-H, 4-H)-$^{19}$F-NMR (CDCl$_3$): δ=−113.5 (ddd, $^2J_{F,F}$=285.6 Hz, $^2J_{F,H}$=57.6 Hz, $^3J_{F,H}$=10.2 Hz), −117.9 (ddd, $^2J_{F,F}$=293.0 Hz, $^2J_{F,H}$=56.5 Hz, $^3J_{F,H}$=12.8 Hz).

80 mg of 17β-difluoromethyl-3-hydroxy-2-methoxy-estra-1,3,5(10)-triene was reacted to form the product according to general synthesis instructions 1 and then purified by flash chromatography (cyclohexane/ethyl acetate=4:1). 82 mg (83%) of 17β-difluoromethyl-2-methoxy-estra-1,3,5(10)-trien-3-yl sulfamate (9) was obtained as colorless crystals.

$^1$H-NMR (CDCl$_3$): δ=0.81 (s, 3H; 18-CH$_3$), 2.79-2.82 (m, 2H; 6-CH$_2$), 3.87 (s, 3H; 2-OCH$_3$), 4.95 (s, 2H; NH$_2$), 5.73 (td, 1H; CHF$_2$), 6.91, 7.03 (2 s, 2H; 1-H, 4-H)-$^{19}$F-NMR (CDCl$_3$): δ=−113.6 (ddd, $^2J_{F,F}$=285.6 Hz, $^2J_{F,H}$=59.1 Hz, $^3J_{F,H}$=11.7 Hz), −117.9 (ddd, $^2J_{F,F}$=285.6 Hz, $^2J_{F,H}$=56.1 Hz, $^3J_{F,H}$=12.8 Hz).

EXAMPLE 10

17β-Carbaldehyde-2-methoxy-estra-1,3,5(10)-trien-3-yl Sulfamate (10)

3.02 g of 3-hydroxy-2-methoxy-estra-1,3,5(10)-trien-17-one was suspended with 4.1 g of trimethylsulfonium iodide in 30 ml of absolute dimethylformamide. At 10° C., 3.5 g of potassium-tert-butylate was added in portions and then slowly heated to room temperature. After 30 minutes, it was poured into ice water and extracted (3×) with ethyl acetate after neutralization with saturated ammonium chloride solution. The combined organic phases were washed with water and then with saturated common salt solution, dried and concentrated by evaporation in a rotary evaporator. 3-Hydroxy-2-methoxy-estra-1,3,5(10)-triene-17β-spiro-1',2'-oxirane was obtained in a quantitative yield (3.19 g) as colorless crystals.

$^1$H-NMR (CDCl$_3$): δ=0.93 (s, 3H; 18-CH$_3$), 2.65, 2.96 (2 d, $^2$J=4.9 Hz, 2H; oxirane-CH$_2$), 3.85 (s, 3H; 2-OCH$_3$), 5.43 (s, 1H; 3-OH), 6.64, 6.77 (2 s, 2H; 1-H, 4-H).

3.19 g of 3-hydroxy-2-methoxy-estra-1,3,5(10)-triene-17β-spiro-1',2'-oxirane and 2 g of sodium azide were suspended in 30 ml of ethylene glycol and heated under argon to 100° C. After 1.5 hours, the solution was cooled off, mixed with saturated ammonium chloride solution and extracted with dichloromethane (3×, altogether 0.25 L). The combined organic phases were washed with water, dried and concentrated by evaporation in a rotary evaporator. After crystallization from ethyl acetate, 17α-azidomethyl-3,17β-dihydroxy-2-methoxy-estra-1,3,5(10)-triene was obtained in a quantitative yield (3.61 g) as a white solid.

$^1$H-NMR (DMSO-D$_6$): δ=0.82 (s, 3H; 18-CH$_3$), 3.09, 3.43 (2 d, $^2$J=12.5 Hz, 2H; CH$_2$N$_3$), 6.45, 6.74 (2 s, 2H; 1-H, 4-H).

3.67 g of 17α-azidomethyl-3,17β-dihydroxy-2-methoxy-estra-1,3,5(10)-triene was suspended in 80 ml of dichloromethane and mixed under argon at room temperature with 3.7 g of triphenylphosphine. After 16 hours, a little water was added and it was concentrated by evaporation in a rotary evaporator and co-evaporated several times with toluene. Flash chromatography of the residue (toluene/ethyl acetate=1:0→20:1) yielded 1.95 g (62%) of an α/β-epimer mixture, from which 1.0 g of 17β-carbaldehyde-2-methoxy-estra-1,3,5(10)-trien-3-ol precipitated from acetone as colorless crystals.

$^1$H-NMR (CDCl$_3$): δ=0.80 (s, 3H; 18-CH$_3$), 3.86 (s, 3H; 2-OCH$_3$), 5.07 (s, 2H; NH$_2$), 5.43 (s, 1H; OH), 6.64, 6.77 (2 s, 2H; 1-H, 4-H), 9.80 (s, 1H; CHO).

125 mg of 17β-carbaldehyde-2-methoxy-estra-1,3,5(10)-trien-3-ol was reacted to form the product according to general synthesis instructions 1 and then purified by flash chromatography (toluene/ethyl acetate=10:1→4:1). 127 mg (81%) of 17β-carbaldehyde-2-methoxy-estra-1,3,5(10)-trien-3-yl sulfamate (10) was obtained as colorless foam.

$^1$H-NMR (DMSO-d$_6$): δ=0.71 (s, 3H; 18-CH$_3$), 3.76 (s, 3H; 2-OCH$^3$), 5.07 (s, 2H; NH$_2$), 6.97, 6.99 (2 s, 2H; 1-H, 4-H), 7.82 (s, 2H; NH$_2$), 9.75 (d, $^3$J=1.6 Hz, 1H; CHO).

EXAMPLE 11

17β-Hydroxymethyl-2-methoxy-estra-1,3,5(10)-trien-3-yl Sulfamate (11)

89 mg of 17β-formyl-2-methoxy-estra-1,3,5(10)-trien-3-ol was dissolved in 2 ml of methanol and 6 ml of tetrahydrofuran and mixed at room temperature with 83 mg of sodium borohydride. After 1 hour, it was mixed with a little acetic acid and silica gel and concentrated by evaporation in a rotary evaporator. Flash chromatography (toluene/ethyl acetate=3:2) yielded 75 mg (84%) of 17β-hydroxymethyl-2-methoxy-esta-1,3,5(10)-trien-3-yl sulfamate (11) as colorless foam.

$^1$H-NMR (DMSO-d$_6$): δ=0.63 (s, 3H; 18-CH$_3$), 3.47-3.52 (m, 1H; CHHOH), 3.76 (s, 3H; 2-OCH$_3$), 4.26 (d, $^2$J=4.7 Hz, 1H; OH), 5.07 (s, 2H; NH$_2$), 6.97 (s, 2H; 1-H, 4-H), 7.81 (s, 2H; NH$_2$).

EXAMPLE 12

2-Methoxy-6-oxo-18a-homoestra-1,3,5(10)-trien-3-yl Sulfamate (12)

3-Acetoxy-2-methoxy-18a-homoestra-1,3,5(10)-triene was oxidized in 6-position with chromium trioxide in acetic acid at 10° C. in a yield of 71%, and then the acetyl group was cleaved off quantitatively by sodium methanolate in methanol. Sulfamoylation of the residue that is obtained according to general synthesis instructions 1 and subsequent flash chromatography (toluene/ethyl acetate=5:1) yielded 2-methoxy-6-oxo-18a-homoestra-1,3,5(10)-trien-3-yl sulfamate (12) in a 90% yield as colorless foam.

$^1$H-NMR (CDCl$_3$): δ=0.81 (t, $^3$J=7.4 Hz, 3H; 18-CH$_3$), 2.44-2.74 (m, 2H; 7-CH$_2$), 3.97 (s, 3H; 2-OCH$_3$), 5.37 (s, 2H; NH$_2$), 6.97, 7.95 (2 s, 2H: 1-H, 4-H).

EXAMPLE 13

2-Methoxy-6-oximino-18a-homoestra-1,3,5(10)-trien-3-yl Sulfamate (13)

61 mg of 2-methoxy-6-oxo-18a-homoestra-1,3,5(10)-trien-3-yl sulfamate (12) was heated with 65 mg of hydroxylamine-hydrochloride and 78 mg of sodium bicarbonate in 3 ml of methanol for 4 hours to 60° C. Then, it was cooled to room temperature, mixed with water and extracted with dichloromethane (3×). The combined organic phases were dried and concentrated by evaporation in a rotary evaporator. Flash chromatography (toluene/acetone=9:1→5:1) yielded 38 mg (60%) of 2-methoxy-6-oximino-18a-homoestra-1,3,5 (10)-trien-3-yl sulfamate (13) as an amorphous solid.

$^1$H-NMR (acetone): δ=0.82 (t, $^3$J=7.4 Hz, 3H; 18-CH$_3$), 3.18 (dd, $^2$J=18.0, $^3$J=4.3 Hz, 1H; 7-CH), 3.90 (s, 3H; 2-OCH$_3$), 6.96 (br s, 2H; NH$_2$), 7.04, 7.89 (2 s, 2H; 1-H, 4-H), 10.07 (s, 1H; OH).

EXAMPLE 14

2-Methoxy-6-(O-methyloximino)18a-homoestra-1,3,5(10)-trien-3-yl Sulfamate (14)

74 mg of 2-methoxy-6-oxo-18a-homoestra-1,3,5(10)-trien-3-yl sulfamate (12) was heated with 158 mg of O-methylhydroxylamine-hydrochloride and 157 mg of sodium bicarbonate in 3 ml of methanol for 3 hours to 70° C. Then, it was cooled to room temperature, mixed with water and extracted with dichloromethane (3×). The combined organic phases were dried and concentrated by evaporation in a rotary evaporator. Flash chromatography (toluene/acetone=14:1→9:1) yielded 59 mg (74%) of 2-methoxy-6-(O-methyloximino)-18a-homoestra-1,3,5(10)-trien-3-yl sulfamate (14) as gray foam.

$^1$H-NMR (CDCl$_3$): δ=0.79 (t, $^3$J=7.4 Hz, 3H; 18-CH$_3$), 3.18 (dd, $^2$J=18.2, $^3$J=4.5 Hz, 1H; 7-CH), 3.91 (s, 3H; NOCH$_3$), 3.95 (s, 3H; 2-OCH$_3$), 5.21 (s, 2H; NH$_2$), 6.90, 7.89 (2 s, 2H; 1-H, 4-H).

EXAMPLE 15

6α-Hydroxy-2-methoxy-18a-homoestra-1,3,5(10)-trien-3-yl Sulfamate (15)

2-Methoxy-6-oxo-18a-homoestra-1,3,5(10)-trien-3-yl sulfamate (12) was dissolved in methanol and mixed in an ice bath with excess sodium borohydride. The ice bath was removed, and after 2 hours, it was mixed with acetone and concentrated by evaporation in a rotary evaporator. The residue was mixed with aqueous ammonium chloride solution and extracted with dichloromethane (3×). The combined organic phases were dried and concentrated by evaporation in a rotary evaporator. Flash chromatography (toluene/ethyl acetate=5:1→3:1) yielded about 50% 6α-hydroxy-2-methoxy-18a-homoestra-1,3,5(10)-trien-3-yl sulfamate (15) as colorless crystals.

$^1$H-NMR (CDCl$_3$): δ=0.78 (t, $^3$J=7.4 Hz, 3H; 18-CH$_3$), 3.87 (s, 3H; 2-OCH$_3$), 4.77 (dd, 1H; 6β-H), 5.32 (s, 2H; NH$_2$), 6.88, 7.44 (2 s, 2H; 1-H, 4-H).

EXAMPLE 16

17α-Fluoro-2-methoxy-estra-1,3,5(10)-trien-3-yl Sulfamate (16)

215 mg of 2-methoxy-estra-1,3,5(10)-triene-3,17β-diol was dissolved in 20 ml of absolute dichloromethane and cooled to −35° C. Then, 280 μl of diethylamino sulfur trifluoride was added, and the cold bath was removed. After 1 hour, it was poured into aqueous sodium bicarbonate solution and extracted with dichloromethane (3×). The combined organic phases were dried and concentrated by evaporation in a rotary evaporator. Flash chromatography (cyclohexane/ethyl acetate=10:1) yielded 49% crude product, which was purified by means of HPLC (Chiracel OD-H 250×4.6 mm; n-heptane/2-propanol=95/5). 46 mg (21%) of 17α-fluoro-3-hydroxy-2-methoxy-estra-1,3,5(10)-triene was obtained as colorless crystals.

$^1$H-NMR (CDCl$_3$): δ=0.70 (d, 3H; 18-CH$_3$), 3.85 (s, 3H; 2-OCH$_3$), 4.57 (dd, J$_{H,F}$=55.3, J$_{H,H}$=5.3 Hz, 1H; 17β-H), 5.46 (s, 1H; OH), 6.64, 6.80 (2 s, 2H; 1-H, 4-H)-$^{19}$F-NMR (CDCl$_3$): δ=−177.25 (ddd, $^2$J=70.4, $^3$J=34.6 and 21.5 Hz).

34 mg of 17α-fluoro-3-hydroxy-2-methoxy-estra-1,3,5(10)-triene was reacted to form the product according to general synthesis instructions 1 and then purified by flash chromatography (toluene/ethyl acetate=12:1→5:1). 42 mg (98%) of 17α-fluoro-2-methoxy-estra-1,3,5(10)-trien-3-yl sulfamate (16) was obtained as an amorphous solid.

$^1$H-NMR (CDCl$_3$): δ=0.71 (d, J=1.6 Hz, 3H; 18-CH$_3$), 2.79-2.82 (m, 2H; 6-CH$_2$), 3.88 (s, 3H; 2-OCH$_3$), 4.58 (dd, J$_{H,F}$=55.5, J$_{H,H}$=5.1 Hz, 1H; 17β-H), 5.29 (s, 2H; NH$_2$), 6.94, 7.04 (2 s, 2H; 1-H, 4-H)-$^{19}$F-NMR (CDCl$_3$): δ=−177.38 (ddd, $^2$J=70.4, $^3$J=34.6 and 19.9 Hz).

EXAMPLE 17

2-Methoxy-(E)-17-(oximino)-estra-1,3,5(10)-trien-3-yl Sulfamate (17)

A suspension of 570 mg of 2-methoxy-17-oxo-estra-1,3,5(10)-trien-3-yl sulfamate, 365 mg of hydroxylamine hydrochloride and 441 mg of sodium bicarbonate in 8 ml of methanol was stirred under reflux for one hour. Then, it was mixed with 30 ml each of water and ethyl acetate. After phase separation, the aqueous phase was extracted twice more with 15 ml each of ethyl acetate. The combined organic phases were first washed with 15 ml of 0.5N HCl and then with saturated NaCl solution, dried on sodium sulfate and concentrated by evaporation in a rotary evaporator. The crude product was purified by flash chromatography (toluene/ethyl acetate 3:1). 444 mg (73%) of 2-methoxy-(E)-17-(oximino)-estra-1,3,5(10)-trien-3-yl sulfamate (17) was obtained as colorless crystals.

$^1$H-NMR (DMSO-d$_6$): δ=0.87 (s, 3H; 13-CH$_3$), 3.76 (s, 3H; 2-OCH$_3$), 6.98, 6.99 (2 s, 2H; 1-H, 4-H), 7.82 (s, 2H; NH$_2$), 10.09 (s, 1H; N—OH):

The invention claimed is:

1. A method of treating a tumor disease which is selected from the group consisting of breast cancer, prostate cancer, colon cancer, non-small-cell-lung cancer and primary dermal microvascular endothelial cell proliferation comprising administering to a subject in need thereof an effective amount of a compound of formula I

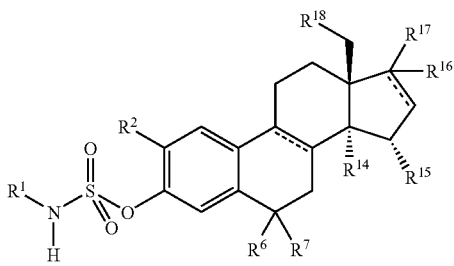

wherein
R$^1$ is hydrogen or C$_1$-C$_5$-alkyl,
R$^2$ is C$_1$-C$_5$-alkoxy, C$_1$-C$_5$-alkyl, or —O—C$_n$F$_m$H$_o$, n=1,2,3,4,5 or 6,
m>1,
m+o=2n+1,
$R^6$ is hydrogen,
$R^7$ is hydrogen, hydroxy, amino, or acylamino, or
$R^6$ and $R^7$ together are an oxygen, oxime or $O(C_1-C_5$-alkyl)-oxime group,
$R^{14}$ and $R^{15}$ are each hydrogen or together a methylene group or an additional bond,
$R^{16}$ is hydrogen, or fluorine,
$R^{17}$ is fluorine, or
if $R^{16}$ is hydrogen, $R^{17}$ is also a CHXY,
X is fluorine, or hydroxyl,
Y is hydrogen or fluorine,
if X is hydroxyl, Y is hydrogen, or
X and Y together can be oxygen,
$R^{18}$ is hydrogen or methyl,
wherein in the B- and D-ring of the compound of formula I, the dotted lines can be up to two double bonds, provided that when a double bond is present in the D ring, only $R^{17}$ is present, or a pharmaceutically acceptable salt thereof.

2. A method according to claim 1, wherein $R^1$ is a hydrogen.

3. A method according to claim 1, wherein $R^2$ is a methyl, ethyl, methoxy, ethoxy or 2,2,2-trifluoroethoxy.

4. A method according to claim 1, wherein $R^6$ and $R^7$ are each a hydrogen or together an oxime group.

5. A method according to claim 1, wherein $R^{14}$ and $R^{15}$ are each an H or together a methylene group.

6. A method according to claim 1, wherein $R^{16}$ is a hydrogen or fluorine.

7. A method according to claim 1, wherein $R^{17}$ is a fluorine, difluoromethyl, carbaldehyde, or hydroxymethyl group.

8. A method according to claim 1, wherein $R^{18}$ is hydrogen.

9. A method according to claim 1, wherein the compound administered is
17β-Difluoromethyl-2-methoxy-estra-1,3,5(10)-trien-3-yl sulfamate;
17-Difluoro-2-methoxy-estra-1,3,5(10),14-tetraen-3-yl sulfamate;
17-Difluoro-2-methoxy-18a-homoestra-1,3,5(10),14-tetraen-3-yl sulfamate;
17β-Carbaldehyde-2-methoxy-estra-1,3,5(10)-trien-3-yl sulfamate;
17β-Carbaldehyde-2-methoxy-18a-homoestra-1,3,5(10)-trien-3-yl sulfamate;
17β-Hydroxymethyl-2-methoxy-estra-1,3,5(10)-trien-3-yl sulfamate;
17α-Fluoro-2-methoxy-estra-1,3,5(10)-trien-3-yl sulfamate;
17β-Fluoro-2-methoxy-estra-1,3,5(10)-trien-3-yl sulfamate;
17-Difluoro-2-methoxy-estra-1,3,5(10)-trien-3-yl sulfamate;
17-Difluoro-2-methoxy-6-oximino-estra-1,3,5(10)-trien-3-yl sulfamate;
17-Difluoro-2-methoxy-18a-homoestra-1,3,5(10)-trien-3-yl sulfamate; or
17-Difluoro-2-methoxy-6-oximino-18a-homoestra-1,3,5(10)-trien-3-yl sulfamate.

10. A method according to claim 1, which is for treating breast cancer.

11. A method according to claim 1, which is for treating prostate cancer.

12. A method according to claim 1, which is for treating colon cancer.

13. A method according to claim 1, which is for treating non-small-cell-lung cancer.

14. A method according to claim 1, which is for treating primary dermal microvascular endothelial cell proliferation.

15. A method according to claim 1, wherein $R^2$ is $C_1-C_5$-alkyl, or a radical $—O—C_nF_mH_o$.

16. A method according to claim 1, wherein $R^7$ is hydroxy, amino, or acylamino, or $R^6$ and $R^7$ together are oxygen, oxime or $O(C_1-C_5$-alkyl)-oxime group.

17. A method according to claim 1, wherein $R^{14}$ and $R^{15}$ are together a methylene group.

18. A method according to claim 1, wherein
$R^{16}$ or $R^{17}$ is fluorine, or
$R^{17}$ is CHXY, wherein
X is a fluorine, or a hydroxyl group, and
Y is a hydrogen atom or a fluorine group.

19. A method according to claim 1, wherein $R^{18}$ is methyl.

20. A method according to claim 1, which is for treating prostate cancer wherein at least one additional active ingredient is administered.

21. A method according to claim 1, wherein the compound administered is
17β-Difluoromethyl-2-methoxy-estra-1,3,5(10)-trien-3-yl sulfamate;
17-Difluoro-2-methoxy-estra-1,3,5(10),14-tetraen-3-yl sulfamate;
17-Difluoro-2-methoxy-18a-homoestra-1,3,5(10),14-tetraen-3-yl sulfamate;
17β-Carbaldehyde-2-methoxy-estra-1,3,5(10)-trien-3-yl sulfamate;
17β-Carbaldehyde-2-methoxy-18a-homoestra-1,3,5(10)-trien-3-yl sulfamate;
17β-Hydroxymethyl-2-methoxy-estra-1,3,5(10)-trien-3-yl sulfamate;
17α-Fluoro-2-methoxy-estra-1,3,5(10)-trien-3-yl sulfamate;
17β-Fluoro-2-methoxy-estra-1,3,5(10)-trien-3-yl sulfamate;
17-Difluoro-2-methoxy-estra-1,3,5(10)-trien-3-yl sulfamate;
17-Difluoro-2-methoxy-6-oximino-estra-1,3,5(10)-trien-3-yl sulfamate;
17-Difluoro-2-methoxy-18a-homoestra-1,3,5(10)-trien-3-yl sulfamate; or
17-Difluoro-2-methoxy-6-oximino-18a-homoestra-1,3,5(10)-trien-3-yl sulfamate or a pharmaceutically acceptable salt thereof.

* * * * *